United States Patent [19]

Gould et al.

[11] 4,345,484

[45] Aug. 24, 1982

[54] SAMPLING DEVICE

[76] Inventors: Gregory Gould, 30 Clairmont Ave., Thornwood, N.Y. 10594; Hendrik Colijn, 423 Franklin Heights Dr., Monroeville, Pa. 15146

[21] Appl. No.: 196,711

[22] Filed: Oct. 14, 1980

[51] Int. Cl.$^3$ .............................................. G01N 1/08
[52] U.S. Cl. .............................. 73/864.43; 73/864.44
[58] Field of Search ........... 73/864.43, 864.44, 864.45; 408/204, 214

[56] References Cited

U.S. PATENT DOCUMENTS

| | | | |
|---|---|---|---|
| 1,386,802 | 8/1921 | Rembert | 73/864.43 |
| 1,927,871 | 9/1933 | Irwin | 73/864.43 |
| 3,447,381 | 6/1969 | Langtry | 73/864.43 |
| 4,179,929 | 12/1979 | Redding | 73/864.43 |

*Primary Examiner*—S. Clement Swisher
*Attorney, Agent, or Firm*—John L. Gray

[57] ABSTRACT

A sampling device comprising a tubular member containing an auger and terminating in a cutting tool is disclosed. The tube is stationary and the auger is rotated by a motor positioned at the upper end of the tube. The cutting tool is located at the bottom end of the tube and is attached to the auger and rotates with it. Provision is made for collecting and holding a sample removed by the auger for ultimate analysis and testing. The entire assembly may be moved vertically for insertion into and removal from the material to be sampled. Because the cutting tool is located on the circumference of the bottom of the tubular member, the cutting tool will cut through and remove a cylindrical core of the material being sampled in such a way tha large loose pieces of material will not be pushed to one side of or fall into the tubular member but will be cut cleanly and a true representative sample of the material being sampled will be obtained.

10 Claims, 4 Drawing Figures

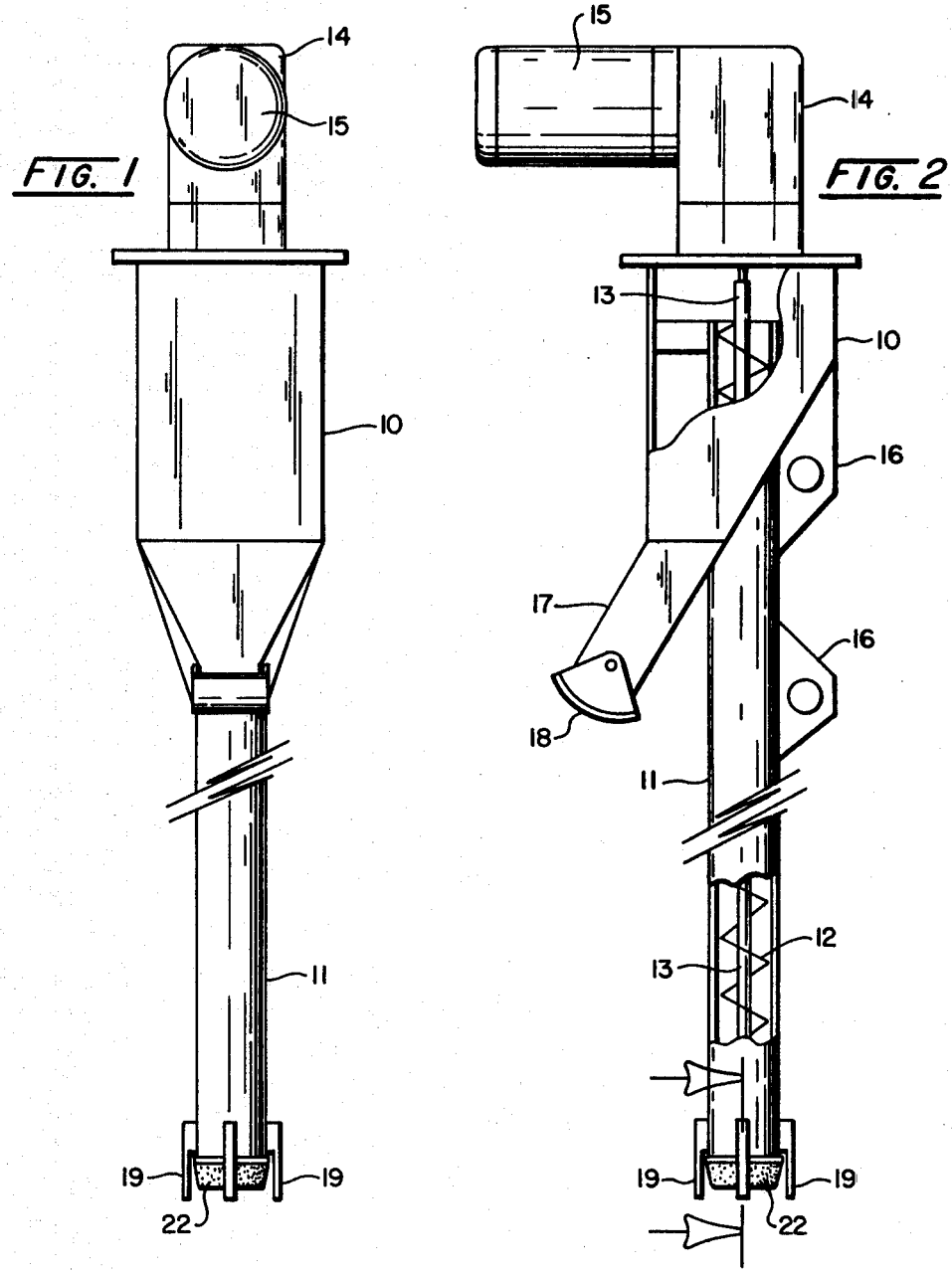

SAMPLING DEVICE

SUMMARY OF THE INVENTION

This invention is concerned with a device for sampling lumpy, bulk heterogeneous materials such as minerals, ores, coal and the like which have been excavated and are in a storage pile or in a suitable container such as a railroad hopper car, a barge, or a ship's hold.

The invention is particularly applicable to the sampling of coal from trucks, railroad hopper cars and barges prior to delivery to the customer, such as a public utility, where it is desirable to get a truly representative sample of the coal.

In general, in sampling, when it is required to measure some property or constituent of a large quantity of anything, a small portion believed to be representative of the entire quantity is collected for testing. Conceptually, the value of a sampling method depends upon the degree of perfection with which the identical composition and attributes of the entire quantity are obtained in the sample.

The sampling of lumpy bulk heterogeneous materials such as coal, minerals, and ores, places demands on the sampling process somewhat apart from those associated with the sampling of discrete units typical of manufactured articles.

In the sampling of bulk heterogeneous materials such as coal, minerals and ores, it is important that every particle in the mass, regardless of relative position, size, shape, hardness, density or other physical characteristics, be neither selectively rejected nor selectively captured in the sampling process. If this condition is not met, a bias error will result and samples will consistently overstate or understate the true value of the whole material being sampled.

Because of the heterogeneous characteristics typical of bulk materials such as coal, minerals, and ores, the sampling of such materials consists of collecting small increments of the sample from throughout the mass and combining them into a single sample which is referred to as a gross sample. This procedure is known as incremental sampling. An increment is defined as that quantity collected by a single motion of a sampling device. The distribution of the sample increments relative to the inherent variations in composition and/or attributes is a potential source of error to the extent that it causes disproportionate representation of composition or other attributes.

Irrespective of any error assignable to selectiveness or distribution in the collection of incremental samples there remains a residual chance error that is operative and the sample value will generally differ from the true value for the whole. This difference is called sampling error. It exclusively governs sampling precision as evidenced by the repeatability of results. The sampling of bulk materials suffers the very special complication that the true value for the whole is unknown. Therefore sampling error is not directly observable and must be determined by statistical techniques.

The performance of a sampling device for the sampling of bulk heterogeneous materials as of and by itself depends exclusively on how well the sampling device executes its function without exhibiting any selectiveness, i.e., any bias that is specific for the sampling device itself.

The overall performance of a sampling process is a function of the device performance, increment distribution and residual or chance error. Chance error can be controlled by the weight or size and number of increments assembled into a gross sample. This latter is well-established in the American Society for Testing and Materials Standard Method for Collection of a Gross Sample of Coal (for example) Specification D-2234.

Bias associated with distribution of the increments is controllable by either uniform or random distribution of increment collection throughout the total mass to be sampled. The remaining bias that is device specific is controllable only by the design of the device.

A major problem encountered in commerce in the sampling of bulk materials is that frequently it must be sampled in situ in trucks, railroad hopper cars, barges, shipholds and storage piles. Control of bias associated with distribution of increments is then comprised to an indeterminate degree by the methods of sampling that are used. In these situations an element of certainty regarding the accuracy of results is lost. The inherent limitations of manual sampling methods for this purpose is universally recognized. Thus devices capable of collecting incremental samples from the interior of such stationary masses in situ have been developed.

Coring as a sample technique has been applied in many fields and the auger is a common device used for this purpose. It has been used for sampling bulk materials also. However, the sampling of heterogeneous loose lumpy materials imposes especially sensitive requirements that the device perform its function completely transparent to variations in physical characteristics of individual particles. Ideally the device should have no tendency selectively to cause individual particles to migrate into or out of the core.

In sampling coal or other ores it is important to withdraw a sample increment that is the exact undisturbed column of material in the location that the sampling device will penetrate. The material so obtained need not be discharged from the sampling device undisturbed but the material collected in the sample increment should contain only the material that had resided in the undisturbed column.

Devices of the prior art for this purpose, such as shown in U.S. Pat. No. 1,927,871, Irwin, and U.S. Pat. No. 4,179,929, Redding, while utilizing an auger and a cutting device attached to the end thereof have no provision for assuring that individual particles will not migrate into or out of the core.

For example, the hand held device of Irwin utilizes a conventional wood drilling screw used for ordinary boring purposes. The leading screw 12 of the Irwin device would, because of its pointed shape and position below the cutting edges 11—11, tend to push pieces of material being sampled out of the undisturbed column of material.

In the case of Redding, the bit at the end of his device is not particularly well disclosed. Reference is made to the fact that it is a conventional bit and it appears to resemble a conventional rotary oil well drilling bit.

It is the specific purpose of the instant invention to prevent such migration by utilizing a circular cutting head at the lower end of the auger which extends around the circumference of the core so as to cut through any particle which is located across the boundary of the core. In this manner, boundary particles are included in the sample increment in proportion to their position relative to the core so that collection of an unbiased increment is assured.

An object of this invention, therefore, is to provide a sampling device which will extract all of the heterogeneous bulk material in the subtended core and not cause any particles to migrate into or out of the core as the sample is obtained.

Another object of this invention is to provide such an incremental sampling device which may be readily inserted into trucks, railroad hopper cars, barges, shipholds, etc., to obtain an incremental sample.

Another object of this invention is to provide a sampling device which can be used to obtain and hold a sample for later discharge into a composite sample.

This, together with other objects and advantages of the invention should become apparent in the details of construction and operation as more fully described hereinafter and claimed, reference being had to the accompanying drawings forming a part hereof wherein like numerals refer to like parts throughout.

BRIEF DESCRIPTION OF THE DRAWINGS

FIG. 1 is a front elevation view of the sampling device.

FIG. 2 is a side elevation view of the sampling device with portions of the covering unit removed to disclose the interior portion.

DETAILED DESCRIPTION OF THE INVENTION

Figure 3:
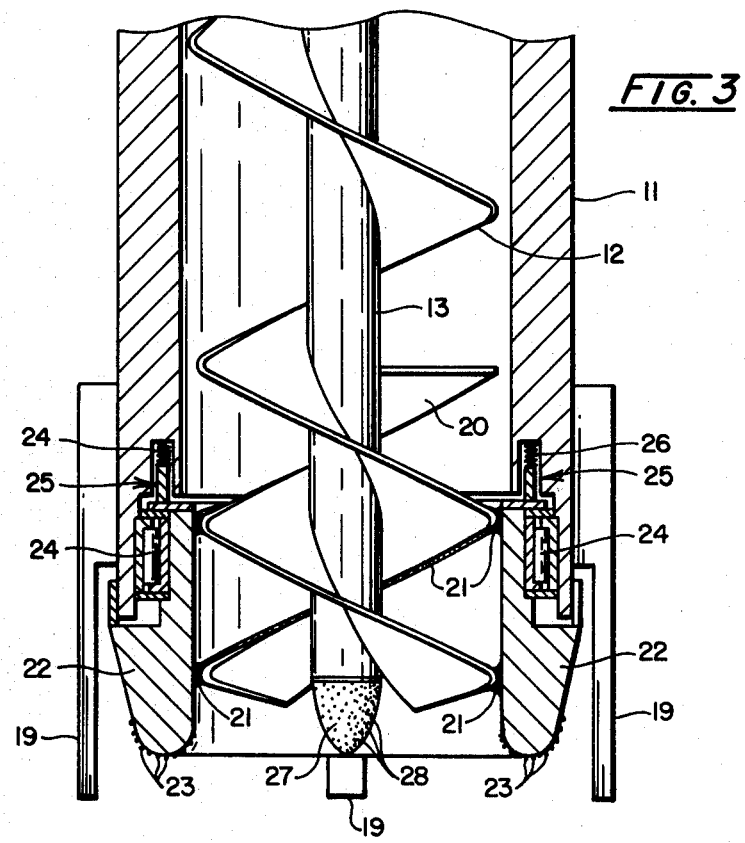
FIG. 3 is a view of the lower portion of the device shown in FIG. 2 partially in section on section line 3—3.

Referring now more particularly to the drawings and to FIGS. 1 and 2, the invention comprises a housing 10. Subtended from the housing 10 is a tubular member 11 containing an auger 12 in the form of an Archimedes' screw mounted on a central shaft 13. This shaft 13 is connected to a drive system which may include suitable gearing (not shown) contained in gear box 14 which is connected to a motor 15. The sampling device is provided with support arms 16—16 which may be connected to a conventional parallelogram structure (not shown) which permits vertical insertion of the sampling device in the heterogeneous bulk material to be sampled. The housing 10 is provided with a discharge chute 17 and a discharge gate 18. The lower portion of the tubular member 11 is provided with legs 19—19 which function is to prevent penetration of the device into the bottom of the container in which the material being sampled is located so that the interior of the container is not damaged by the device when it reaches the lower limit of the material being sampled.

Figure 4:
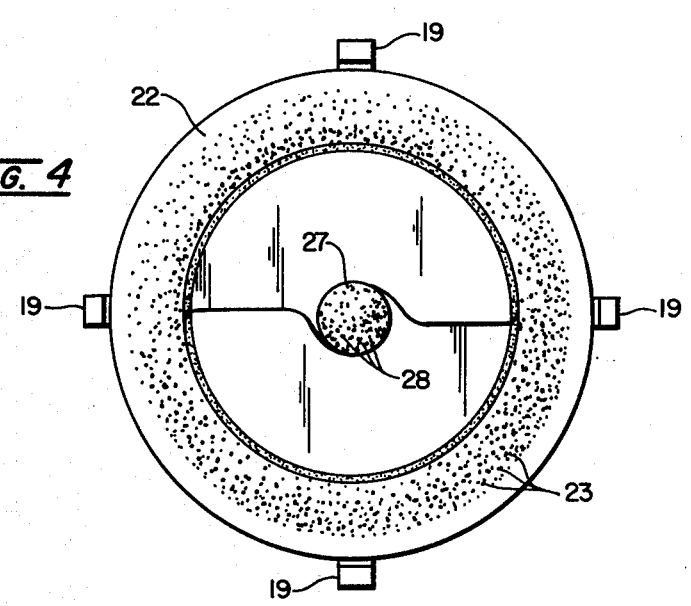
FIG. 4 is a vertical view of the device from the lower end thereof.

Referring now more particularly to FIGS. 3 and 4, the lower portion of the shaft 13 is provided with a second auger flight 20 for additional strength and improved material removal. Attached to the lower auger portion of weldments 21—21 is a circumferential cutter 22 which is surfaced with cutting particles 23—23 such as diamond or tungsten carbide chips. If desired, cutter 22 may be provided with teeth (not shown) which, in turn, may be surfaced with a hardened material on all or a portion thereof. Bearings 24—24 are provided for rotation of the circumferential cutter 22 and a sealing ring 25 which is held from the tube 11 by means of springs 26—26 is located at the upper end of the circumferential cutter 22. The lower end of the shaft 13 may also be provided with a cutting element 27 also surfaced with cutting particles 28—28 such as diamond or tungsten carbide chips. This cutting element 27 is relatively blunt and preferably does not extend lower than circumferential cutter 22 since its purpose is to break up large pieces of the product being sampled to facilitate their transport up the auger 12 and not to pull the unit down through the material being sampled, as in the case of a conventional wood drill.

For coal sampling, for example, the overall diameter of tube 11 is typically six inches and the shaft rotates at approximately 300 to 400 rpms.

In operation, the sampling device is inserted vertically into the bulk heterogeneous material being sampled, such as coal in a hopper car or a barge, and the rotating shaft 13 causes the cutting edge 22 to cut through the coal and remove all pieces of material being sampled in that incremental core unit. The pieces are further broken up by the optional cutting head 27 and raised to the upper housing 10 of the device by means of the auger 12 and held in the collection tube 17 and housing 10 for eventual combining with other samples by discharge through gate 18. Thus, all of the particles in the hypothetical tubular portion to be retrieved are retrieved with no particles migrating out of the tubular area or into it.

In some instances, it may be desirable to arrange a plurality of the above described coal sampling devices ganged together so that multiple samples are obtained upon actuation of the parallelogram structure referred to above.

While this invention has been described in its preferred embodiment, it is appreciated that variations therefrom may be made without departing from the proper scope and spirit of the invention.

What is claimed is:

1. A sampling device comprising a tubular means, auger means rotatable within said tubular means, cutting means attached to said auger means, said cutting means comprising circular cutting means having a circumference approximately equal to the circumference to said tubular means.

2. The sampling device of claim 1 wherein a housing is provided at the upper end of said tubular means adapted to receive material being sampled by said sampling device.

3. The sampling device of claim 2 wherein a drive system is provided at the upper end of said tubular means attached to said auger to provide its rotation.

4. The sampling device of claim 3 wherein said auger means extends throughout the length of said tubular means and is provided with said cutting means at the end opposite to said end attached to said motor.

5. The sampling device of claim 1 wherein said circular cutting means is annular in shape, having an external circumference approximately equal to the external circumference of said tubular means and having a cross sectional thickness approximately the same as the thickness of the wall of said tubular means.

6. The sampling device of claim 1 wherein said auger means is provided with a separate cutting means attached to the center thereof and centrally located with respect to said cutting means.

7. A sampling device comprising a housing adapted to receive and temporarily hold material gathered by said sampling device, a hollow cylindrical tube attached to said housing and extending downwardly therefrom, a shaft mounted within said tube, means for rotating said shaft attached thereto and mounted on said housing, at least one continuous Achimedes' screw at the lower end thereof and having an external circumference approximately equal to that of said tube.

8. The sampling device of claim 7 wherein said shaft is provided with a blunt abrasive cutter at the lower end thereof.

9. The sampling device of claim 8 wherein said blunt abrasive cutter on the lower end of said shaft is approximately the same elevation as the said annular cutting device.

10. The sampling device of claim 9 wherein said shaft is provided with an Archimedes' screw attached to and extending approximately its entire length and a second Archimedes' screw extending a portion of its length, said abrasive cutter being attached to both Archimedes' screws outer sections at the lower ends thereof.

* * * * *

UNITED STATES PATENT AND TRADEMARK OFFICE
CERTIFICATE OF CORRECTION

PATENT NO. : 4,345,484
DATED : August 24, 1982
INVENTOR(S) : Gregory Gould et al.

It is certified that error appears in the above-identified patent and that said Letters Patent is hereby corrected as shown below:

On The Title Page,

Abstract line 14, "tha" should resd -- that --.

Column 3, line 57, "of" should read -- by --.

Column 4, line 40, "to" should resd -- of --.

Signed and Sealed this

Twenty-sixth Day of October 1982

[SEAL]

Attest:

GERALD J. MOSSINGHOFF

Attesting Officer

Commissioner of Patents and Trademarks